United States Patent
Lu et al.

(10) Patent No.: US 9,493,554 B2
(45) Date of Patent: *Nov. 15, 2016

(54) METHODS OF TREATING RETINAL DISORDERS WITH ANTI-APELIN ANTIBODIES

(71) Applicant: AMGEN INC., Thousand Oaks, CA (US)

(72) Inventors: Shu-Chen Lu, Thousand Oaks, CA (US); Minghan Wang, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,662

(22) Filed: Aug. 28, 2015

(65) Prior Publication Data

US 2016/0053000 A1     Feb. 25, 2016

Related U.S. Application Data

(63) Continuation of application No. 14/233,364, filed as application No. PCT/US2012/047048 on Jul. 17, 2012, now Pat. No. 9,156,911.

(60) Provisional application No. 61/508,862, filed on Jul. 18, 2011.

(51) Int. Cl.

| | |
|---|---|
| A61P 35/00 | (2006.01) |
| A61P 27/02 | (2006.01) |
| A61K 39/395 | (2006.01) |
| C07K 16/18 | (2006.01) |
| G01N 33/53 | (2006.01) |
| C12P 21/02 | (2006.01) |
| C12N 15/09 | (2006.01) |
| C12N 15/11 | (2006.01) |
| C07H 21/02 | (2006.01) |
| C07K 16/26 | (2006.01) |
| G01N 33/74 | (2006.01) |
| A61K 9/00 | (2006.01) |
| C07K 14/47 | (2006.01) |
| C07K 14/515 | (2006.01) |
| A61K 39/00 | (2006.01) |

(52) U.S. Cl.
CPC ............ *C07K 16/18* (2013.01); *A61K 9/0019* (2013.01); *A61K 9/0048* (2013.01); *A61K 39/395* (2013.01); *A61K 39/3955* (2013.01); *C07H 21/02* (2013.01); *C07K 16/26* (2013.01); *C12N 15/09* (2013.01); *C12N 15/11* (2013.01); *C12P 21/02* (2013.01); *G01N 33/53* (2013.01); *G01N 33/74* (2013.01); *A61K 2039/505* (2013.01); *C07K 14/515* (2013.01); *C07K 2317/34* (2013.01); *C07K 2317/76* (2013.01); *C07K 2317/92* (2013.01); *G01N 2800/7014* (2013.01)

(58) Field of Classification Search
None
See application file for complete search history.

(56) References Cited

U.S. PATENT DOCUMENTS

| | | | |
|---|---|---|---|
| 7,736,646 B2 | 6/2010 | Krieg | |
| 9,156,911 B2 * | 10/2015 | Lu | ............... C07K 16/26 |
| 2006/0159676 A1 | 7/2006 | Krieg | |
| 2009/0265797 A1 | 10/2009 | Goetsch et al. | |

FOREIGN PATENT DOCUMENTS

WO      2004/081198 A2     9/2004

OTHER PUBLICATIONS

Sandhu, 1992. Critical Reviews in Biotechnology. 12(5/6):437-462.*
Casset et al. (2003), "A peptide mimetic of an anti-CD4 monoclonal antibody by rational design", Biochem. Biophys. Res. Comm., 307(1):198-205.
Chen et al. (1999), "Selection and analysis of an optimized anti-VEGF antibody: crystal structure of an affinity-matured fab in complex with antigen", J. Mol. Biol., 293(4):865-881.
Holm et al. (2007), "Functional mapping and single chain construction of the anti-cytokeratin 8 monocolonal antibody TS1", Mol. Immunol., 44(6):1075-1084.
Kasai, Atsushi et al. (Oct. 2008), "Retardation of retinal vascular development in apelin-deficient mice", Arterioscler. Thromb. Vasc. Biol., 28:1717-1722.
Kasai, Atsushi et al. (Nov. 2010), "Apelin is a crucial factor for hypoxia-induced retinal angiogenesis", Arterioscler. Thromb. Vasc. Biol., 30(11):2182-2187.
Kaufman et al. (1999), "Transgenic analysis of a 100-kb human beta-blogin cluster-containing DNA fragment propagated as a bacterial artificial chromosome", Blood, 94(9):3178-3184.
MacCallum et al. (1996), "Antibody-antigen interactions: contact analysis and binding site topography", J. Mol. Biol., 262(5):732-745.
Pascalis et al. (2002), "Grafting of 'abbreviated' complementarity-determining regions containing specificity-determining residues essential for ligand contact to engineer a less immunogenic humanized monoclonal antibody", J. Immunol., 169(6):3076-3084.
Rayalam, Srujana et al. (Feb. 2008), "A putative role for apelin in the etiology of obesity", Biochem. Biophys. Res. Comm., 368(3):815-819.
Rayalam, Srujana et al. (Sep. 2011), "Emerging role of apelin as a therapeutic target in cancer: a patent review", Recent Patents on Anti-Cancer Drug Disc., 6(3): 367-372.
Reaux, Annabelle et al. (May 2001), "Physiological role of a novel neuropeptide, apelin, and its receptor in the rat brain", J. Neurochem., 77(4):1085-1096.

(Continued)

*Primary Examiner* — Zachary Howard
(74) *Attorney, Agent, or Firm* — Lisa E. Alexander

(57) ABSTRACT

This disclosure relates to apelin antigen-binding proteins and methods of using the apelin antigen-binding proteins. The antigen-binding protein may comprise an antibody to apelin and can be used to treat pathological conditions involving angiogenesis. The pathological conditions can comprise cancer or retinopathy and/or retinopathy-related complications.

19 Claims, 7 Drawing Sheets

(56) References Cited

OTHER PUBLICATIONS

Rudikoff et al. (1982), "Single amino acid substitution altering antigen-binding specificity", PNAS, 79(6):1979-1983.

Tao, Yong et al. (Aug. 2010), "Apelin in plasma and vitreous and in fibrovascular retinal membranes of patients with proliferative diabetic retinopathy", Invest. Opthamol. Vis. Sci., 51(8):4237-4242.

Vajdos et al. (2002), "Comprehensive functional maps of the antigen-binding site of an anti-erbB2 antibody obtained with shotgun scanning mutagenesis", J. Mol. Biol., 320(2):415-428.

Wang et al. (1999), "Rapid analysis of gene expression (RAGE) facilitates universal expression profiling", Nuc. Acids Res., 27(23):4609-4618.

Wu et al. (1999), "Humanization of a murine monoclonal antibody by simultaneous optimization of framework and CDR residues", J. Mol. Biol., 294(1):151-162.

* cited by examiner

FIG. 1

\>LC
<u>mdsqaqvlillllwvsgtcg</u>
divmsqspsslavsagekvtmsc *kssqslldsrtrknyla* wyqqkpgqspkllis *wasires*
gvpdrftgsgsgtdftlsissvqaedlavyyc *kqsyyllt* fgagtklelkr
(SEQ ID NO: 1)

divmsqspsslavsagekvtmsc *kssqslldsrtrknyla* wyqqkpgqspkllis *wasires*
gvpdrftgsgsgtdftlsissvqaedlavyyc *kqsyyllt* fgagtklelkr
(SEQ ID NO: 2)

CDR 1   kssqslldsrtrknyla  (SEQ ID NO: 23)

CDR 2   wasires (SEQ ID NO: 24)

CDR 3   kqsyyllt (SEQ ID NO: 25)

\>HC
<u>MNFGLSLIFLVLVLKGVQC</u>
NVQLVESGGGLVKPGGSLKLSCVASGFIFS *DYVMS* WVRQTPEKRLEWVA
*TISDGGIYTSYPDNIKG* RFTISRDNANNKLYLQMSHLRSEDTAMYFCSR
*AAITSDDFDF* WGQGTALTVSS                                     (SEQ ID NO: 26)

NVQLVESGGGLVKPGGSLKLSCVASGFIFS *DYVMS* WVRQTPEKRLEWVA
*TISDGGIYTSYPDNIKG* RFTISRDNANNKLYLQMSHLRSEDTAMYFCSR
*AAITSDDFDF* WGQGTALTVSS                                     (SEQ ID NO: 27)

CDR 4   DYVMS  (SEQ ID NO: 28)

CDR 5   TISDGGIYTSYPDNIKG  (SEQ ID NO: 29)

CDR 6   AAITSDDFDF  (SEQ ID NO: 30)

FIG. 2A

| 1 | apelin 13 | QRPRLSHKGPMPF | SEQ ID NO: 7 |
| 2 | apelin 13 C-blot | QRPRLSHKGPMPF | SEQ ID NO: 8 |
| 3 | pyro13 C-blot | pGluRPRLSHKGPMPF | SEQ ID NO: 9 |
| 4 | F13A | QRPRLSHKGPMPA | SEQ ID NO: 10 |
| 5 | apelin 12 | RPRLSHKGPMPF | SEQ ID NO: 11 |
| 6 | apelin 11 | PRLSHKGPMPF | SEQ ID NO: 12 |
| 7 | apelin 10 | RLSHKGPMPF | SEQ ID NO: 13 |
| 8 | apelin 9 | LSHKGPMPF | SEQ ID NO: 14 |
| 9 | apelin 8 | SHKGPMPF | SEQ ID NO: 15 |
| 10 | apelin 7 | HKGPMPF | SEQ ID NO: 16 |
| 11 | apelin 12-2 | RPRLSHKGPMP | SEQ ID NO: 17 |
| 12 | apelin 12-3 | RPRLSHKGPM | SEQ ID NO: 18 |
| 13 | apelin 12-4 | RPRLSHKGP | SEQ ID NO: 19 |
| 14 | apelin 12-5 | RPRLSHKG | SEQ ID NO: 20 |
| 15 | apelin 12-6 | RPRLSHK | SEQ ID NO: 21 |
| 16 | apelin 27-14 | GPGAWQGGRRKFRR | SEQ ID NO: 22 |

FIG. 2B

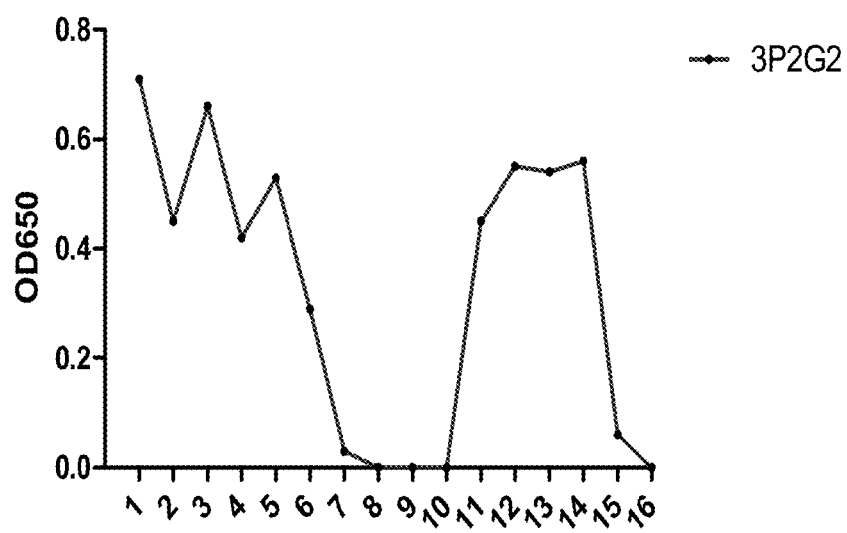

anti apelin mAb ELISA

FIG. 5

```
                    (1) 1         10        20        30        40        50        60         77
NP059109 human  (1) MNLRLCVQALLLLWLSLTAVCGGSLMPLPDGNGLEDGNVRHLVQPRGSRNGPGPWQGGRRKFRRQRPRLSHKGPMPF
NP038940 mouse  (1) MNLRLCVQALLLLWLSLTAVCGVPIMLPPDGTGLEEGSMRYLVKPRTSRTGPGAWQGGRRKFRRQRPRLSHKGPMPF
NP113800 rat    (1) MNLSFCVQALLLLWLSLTAVCGVPIMLPPDGKGLEEGNMRYLVKPRTSRTGPGAWQGGRRKFRRQRPRLSHKGPMPF
NP776928 Bovine (1) MNLRRCVQALLLLWLCLSAVCGGPLLQTSDGKEMEEGTLRYLVQPRGPRSGPGPWQGGRRKFRRQRPRLSHKGPMPF
```

METHODS OF TREATING RETINAL DISORDERS WITH ANTI-APELIN ANTIBODIES

CROSS REFERENCE TO RELATED APPLICATIONS

This application is a continuation of U.S. application Ser. No. 14/233,364, filed Mar. 26, 2014, which is a national phase entry of International Application No. PCT/US2012/047048, filed Jul. 17, 2012, which claims the benefit of U.S. Provisional Application No. 61/508,862, filed Jul. 18, 2011, all of which are hereby incorporated by reference in their entireties.

SEQUENCE LISTING

The present application is being filed along with a Sequence Listing in electronic format. The Sequence Listing is provided as a file entitled "A-1633-US-CNT_ST25.txt" and was created on Aug. 28, 2015. The text file is 12,062 bytes in size. The information in the electronic format of the Sequence Listing is incorporated herein by reference in its entirety.

FIELD OF THE INVENTION

This disclosure relates to apelin antigen-binding proteins and methods of using the apelin antigen-binding proteins. The antigen-binding protein may comprise an antibody to apelin.

BACKGROUND OF THE INVENTION

Apelin is an endogenous ligand for the angiotensin-1-like receptor APJ. Apelin is derived from a 77 amino acid precursor and processed into several active molecular forms including apelin-12, apelin-13, apelin-17 and apelin-36. Apelin is expressed in various organs, e.g. heart, lung, kidney, liver and other tissues. Apelin and the apelin receptor (APJ) are a G-protein coupled receptor system that has been found to be involved in pathological conditions involving angiogenesis, including cancer. Recently, apelin has been reported to be involved in hypoxia-induced retinal angiogenesis (Kasai et al. Arterioscler Thromb Vasc Biol 2010: 30, 2182-2187). It has also been reported that certain compositions may inhibit angiogenesis by inhibiting the apelin/APJ pathway (U.S. Pat. No. 7,736,646).

Apelin knockout mice have been shown to have impaired retinal vascularization and ocular development (Kasai et al. Arterioscler Thromb Vasc Biol 2008: 28, 1717-1722). The impaired vascular development occurred at least in the early postnatal period. Furthermore, it was suggested that apelin/APJ signaling was involved in a cooperative manner with VEGF or FGF2 in this condition.

It has also been reported that vitreous concentrations of apelin were significantly higher in patients having proliferative diabetic retinopathy (Tao et al., Invest Opthamol Visual Science 2010: 51, 4237-4242).

SUMMARY OF THE INVENTION

The invention relates to antigen-binding proteins that bind to apelin and fragments thereof. In various embodiments the antigen-binding proteins are antibodies. Additionally, uses are provided for the antigen-binding proteins described herein.

In various embodiments the isolated antigen-binding protein comprises a light chain (SEQ ID NO: 2) and a heavy chain (SEQ ID NO: 27). In other embodiments, the antigen-binding protein can comprise a polypeptide of only SEQ ID NO: 2 or SEQ ID NO: 27. In other aspects the antigen-binding protein sequence can be about 95%, about 96%, about 97%, about 98%, about 99% identical to SEQ ID NOs: 2 or 27. The antigen-binding protein can be a monoclonal antibody or fragment thereof. In certain embodiments, the antibody can be a mouse antibody, a humanized antibody, a chimeric antibody, a multispecific antibody, or fragment of a mouse antibody, a humanized antibody, a chimeric antibody or a multispecific antibody. In various embodiments, the antigen-binding protein specifically binds to an apelin polypeptide comprising the sequence QRPRLSHKGPMPF (SEQ ID NO: 31) or PRLSHKG (SEQ ID NO: 32) or a full-length human (SEQ ID NO: 3), mouse (SEQ ID NO: 4), rat (SEQ ID NO: 5) or bovine sequence (SEQ ID NO: 6).

In yet other embodiments the antigen-binding protein can have a $K_D$ of 6 nM or less. The antigen binding protein can also be a neutralizing antibody. Other embodiments can comprise a nucleic acid sequence encoding any of the above antigen-binding proteins. In various embodiments, the antigen binding protein can inhibit angiogenesis. The angiogenesis can be inhibited in cancer or diabetic retinopathy and/or retinopathy-associated complications. Inhibition of angiogenesis can be measured in vitro by decreased length during tube formation.

In various embodiments the isolated antigen-binding protein comprises a polypeptide having the sequences of SEQ ID NO: 23, SEQ ID NO: 24, SEQ ID NO: 25, SEQ ID NO: 28, SEQ ID NO: 29 and SEQ ID NO: 30. In some embodiments the isolated antigen binding protein can comprise only one, two, three, four or five of the SEQ ID NOs: 23-30. In other aspects the antigen-binding protein sequence can be about 95%, about 96%, about 97%, about 98%, about 99% identical to SEQ ID NO: 23, SEQ ID NO: 24, SEQ ID NO: 25, SEQ ID NO: 28, SEQ ID NO: 29 or SEQ ID NO: 30. The antigen-binding protein can be a monoclonal antibody or fragment thereof. In certain embodiments, the antibody can be a mouse antibody, a humanized antibody, a chimeric antibody, a multispecific antibody, or fragment of a mouse antibody, a humanized antibody, a chimeric antibody or a multispecific antibody. In various embodiments, the antigen-binding protein specifically binds to a polypeptide comprising the sequence QRPRLSHKGPMPF (SEQ ID NO: 31) or PRLSHKG (SEQ ID NO: 32) or a full-length human, mouse, rat or bovine sequence (SEQ ID NOs: 3-6).

In yet other embodiments the antigen-binding can have a $K_D$ of 6 nM or less. The antigen binding protein can also be a neutralizing antibody. Other embodiments can comprise a nucleic acid sequence encoding any of the above antigen-binding proteins. In various embodiments, the antigen binding protein can inhibit angiogenesis. The angiogenesis can be inhibited in diabetic retinopathy or cancer. The inhibition of angiogenesis can be measured in vitro by decreased length during tube formation.

In various embodiments the invention relates to an expression vector comprising a nucleic acid encoding any of the above antigen-binding proteins. The expression vector can be placed in a host cell. The host cell can comprise the nucleic acid and the host cell can be a eukaryotic or prokaryotic cell. In various embodiments the eukaryotic host cell can be a mammalian cell. In certain embodiments a method of producing an antibody is provided. The method can comprise culturing the host cell under suitable conditions such that the nucleic acid is expressed to produce the antibody. The antibody can then be recovered from the culture of the host cell.

In various embodiments, a pharmaceutical composition is provided comprising any of the above antigen-binding proteins and a pharmaceutically acceptable carrier, diluent or excipient.

In yet other embodiments a method for detecting the presence of apelin in a biological sample is provided. The method can comprise incubating the sample with at least one of the antigen-binding protein set forth above under conditions that allow binding of the antigen-binding protein to apelin, and detecting the bound antigen-binding protein or apelin. In various embodiments a method of treating a disorder associated with increased angiogenesis in a mammal in need of treatment is provided. The method can comprise administering any of the above antigen-binding proteins or the above pharmaceutical composition to the mammal. The disorder can comprise hemangioma, solid tumors, leukemias, lymphomas, myelomas, plaque neovascularization, corneal diseases, rubeosis, neovascular glaucoma, retinopathy, exudative age-related macular degeneration (AMD), proliferative diabetic retinopathy (PDR), diabetic macular edema (DME), neovascular glaucoma, corneal neovascularization (trachoma), pterygium, diabetic retinopathy, retrolental fibroplasia, diabetic neovascularization, macular degeneration, uterine bleeding, endometrial hyperplasia and carcinoma, endometriosis, myometrial fibroids (uterine leiomyomas) and adenomyosis, ovarian hyperstimulation syndrome, tumorigenesis or cancer.

BRIEF DESCRIPTION OF THE DRAWINGS

FIG. 1. This figure presents the sequence of the light chain and heavy chain of antibody A (Ab A) to apelin. The CDR regions in the heavy and light chains are shown in bold, italic type. The signal sequences are underlined. Additionally, the individual CDR's are presented.

FIGS. 2A-B. These figures provide the individual apelin peptides (FIG. 2A) that were tested against Ab A and also show an anti-apelin mAb ELISA of the antibody and the apelin peptides (FIG. 2B)

FIG. 4A demonstrates the effect of apelin on tube formation which is an indication of angiogenesis. FIG. 4B demonstrates inhibition of angiogenesis when Ab A is added with apelin.

FIG. 5. This figure presents the full-length sequence of mouse, rat, human and bovine apelin. The NP059109 human sequence is SEQ ID NO: 3. The NP038940 mouse sequence is SEQ ID NO: 4. The NP113800 rat sequence is SEQ ID NO: 5. The NP776928 bovine sequence is SEQ ID NO: 6.

DETAILED DESCRIPTION

Figure 3:
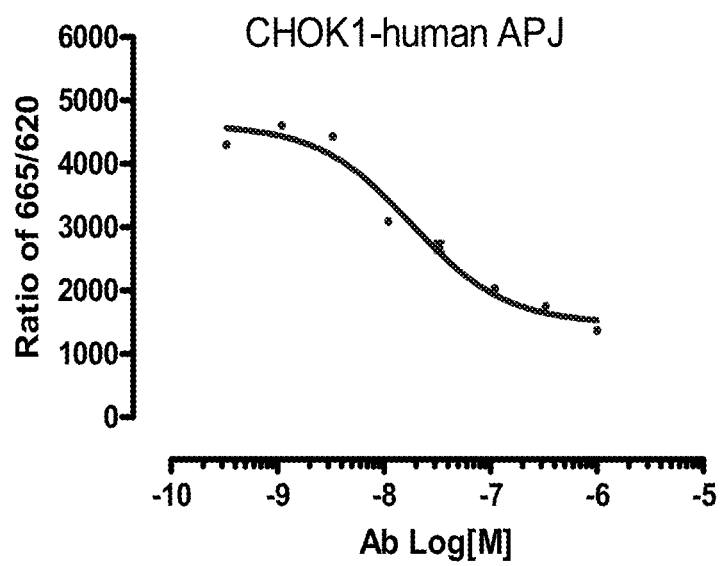
FIG. 3. This figure presents the results of a neutralization assay with apelin and Ab A.

Apelin antigen-binding proteins (such as antibodies and functional binding fragments thereof) that bind to apelin are disclosed herein. In some embodiments, the antigen-binding proteins bind to apelin and prevent apelin from functioning in various ways. For example, the apelin binding proteins may inhibit angiogenesis and more specifically, the angiogenesis associated with cancer, retinopathy and/or retinopathy-related complications. The retinopathy can be diabetic retinopathy. Alternatively, the apelin binding proteins may inhibit angiogenesis in tumors or other forms of cancer.

The foregoing summary is not intended to define every aspect or embodiment of the invention, and additional aspects may be described in other sections. The entire document is intended to be related as a unified disclosure, and it should be understood that all combinations of features described herein may be contemplated, even if the combination of features is not found together in the same sentence, or paragraph, or section of this document.

In addition to the foregoing, as an additional aspect, all embodiments narrower in scope in any way than the variations defined by specific paragraphs herein can be included in this disclosure. For example, certain aspects are described as a genus, and it should be understood that every member of a genus can be, individually, an embodiment. Also, aspects described as a genus or selecting a member of a genus should be understood to embrace combinations of two or more members of the genus. It should also be understood that while various embodiments in the specification are presented using "comprising" language, under various circumstances, a related embodiment may also be described using "consisting of" or "consisting essentially of" language.

It will be understood that the descriptions herein are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

It should also be understood that when describing a range of values, the characteristic being described could be an individual value found within the range. For example, "a pH from about pH 4 to about pH 6," could be, but is not limited to, pH 4, 4.2, 4.6, 5.1 5.5 etc. and any value in between such values. Additionally, "a pH from about pH 4 to about pH 6," should not be construed to mean that the pH in question varies 2 pH units from pH 4 to pH 6, but rather a value may be picked from within a two pH range for the pH of the solution.

In some embodiments, when the term "about" is used, it means the recited number plus or minus 5%, 10%, 15% or more of that recited number. The actual variation intended is determinable from the context.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the disclosure, the following terms, unless otherwise indicated, shall be understood to have the following meanings:

An antibody or antigen-binding fragment can be an agonist or an antagonist.

An "agonist" refers to an agent that binds to a polypeptide (such as a receptor), or a polynucleotide and stimulates, increases, activates, facilitates, enhances activation, sensitizes or up regulates the activity or expression of the polypeptide or polynucleotide.

An "antagonist" refers to an agent that inhibits expression of a polypeptide or polynucleotide or binds to, partially or totally blocks stimulation, decreases, prevents, delays activation, inactivates, desensitizes, or down regulates the activity of the polypeptide or polynucleotide.

"Angiogenesis" should be understood to mean the growth of new blood vessels. Angiogenesis may occur under conditions of normal or abnormal growth (e.g tumor growth). Angiogenesis may also be referred to as vasculogenesis or arteriogenesis Inhibition of angiogenesis should be understood to occur when administration of an angiogenesis inhibitor (e.g. an anti-apelin antibody) is administered in vivo or provided to an in vitro assay system and there is a decrease in blood vessels or an indicator of blood vessel growth. In an in vitro system, the inhibition may be reflected as a decrease in the length of a structure called a "tube" structure. For example, an in vitro angiogenesis assay can be measured using Cellplayer GFP AngioKit-96 (Essen Bioscience). The assay measures both positive and negative effects on tube (vessel) formation during angiogenesis when human endothelial cells are co-cultures with other human cells.

The term "polynucleotide" or "nucleic acid" includes both single-stranded and double-stranded nucleotide polymers. Nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are about 10 to about 60 bases in length. In other embodiments, oligonucleotides are about 12, about 13, about 14, about 15, about 16, about 17, about 18, about 19, or about 20 to about 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

An isolated nucleic acid can encode antigen-binding proteins disclosed in various embodiments herein, e.g. an apelin antigen-binding protein or anti-apelin antibody. The nucleic acid is said to be "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "amino acid" refers to natural and/or non-naturally occurring amino acids, and includes its normal meaning in the art.

The terms "polypeptide" or "protein" means a macromolecule having the amino acid sequence of a native protein, i.e., a protein produced by a naturally-occurring and non-recombinant cell; or the protein can be produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass inter alia, apelin antigen-binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In various embodiments, fragments can be about five to about 500 amino acids long. For example, fragments can be at least about 5, about 6, about 8, about 10, about 14, about 20, about 50, about 70, about 100, about 150, about 200, about 250, about 300, about 350, about about 400, or about 450 amino acids long. Useful polypeptide fragments include immunologically functional fragments of antibodies, including binding domains. In the case of an apelin-binding antibody, useful fragments include but are not limited to a CDR region, a variable domain of a heavy and/or light chain, a portion of an antibody chain or just its variable region including one, two, three, four, five or six CDRs, and the like.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or non-covalent interaction) with a polypeptide with which it is not associated in nature, or (6) does not occur in nature. Typically, an "isolated protein" constitutes at least about 5%, at least about 10%, at least about 25%, or at least about 50%, at least about 75%, at least about 90% or more of a given sample. Genomic DNA, cDNA, mRNA or other RNA, of synthetic origin, or any combination thereof can encode such an isolated protein. In various embodiments, the isolated protein is substantially free from proteins or polypeptides or other contaminants that are found in its natural environment that would interfere with its therapeutic, diagnostic, prophylactic, research or other use.

A "variant" of a polypeptide (e.g., an antigen-binding protein, or an antibody) comprises an amino acid sequence wherein one or more amino acid residues are inserted into, deleted from and/or substituted into the amino acid sequence relative to another polypeptide sequence. Variants include fusion proteins.

As used herein, the twenty conventional (e.g., naturally occurring) amino acids and their abbreviations follow conventional usage. See *Immunology—A Synthesis* (2nd Ed., E. S. Golub & D. R. Gren, Eds., Sinauer Assoc., Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for polypeptides of various embodiments described herein. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:

Hydrophobic: Norleucine, Met, Ala, Val, Leu, Ile;
Neutral hydrophilic: Cys, Ser, Thr, Asn, Gln;
Acidic: Asp, Glu;
Basic: His, Lys, Arg;
Residues that influence chain orientation: Gly, Pro; and
Aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to an antigen-binding protein (such as an antibody), according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |

TABLE 1-continued

Amino Acid Substitutions

| Original Residues | Exemplary Substitutions | Preferred Substitutions |
|---|---|---|
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen-binding protein can have a greater circulating half-life than an antigen-binding protein that is not chemically modified. In certain embodiments, a chemically modified antigen-binding protein can have improved targeting capacity for desired cells, tissues, and/or organs. In some embodiments, a derivative antigen-binding protein is covalently modified to include one or more water soluble polymer attachments, including, but not limited to, polyethylene glycol, polyoxyethylene glycol, or polypropylene glycol. See e.g., U.S. Pat. Nos. 4,640,835, 4,496,689, 4,301,144, 4,670,417, 4,791,192 and 4,179,337. In certain embodiments, a derivative antigen-binding protein comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen-binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by at least one linkage selected from: —$CH_2NH$—, —$CH_2S$—, —$CH_2$—$CH_2$—, —CH=CH-(cis & trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo & Gierasch, Ann. Rev. Biochem., 61:387 (1992), incorporated herein by reference for any purpose); for example, by adding internal cysteine residues capable of forming intramolecular disulfide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, about 65%, about 70%, about 75%, about 80%, about 85%, about 90%, about 91%, about 92%, about 93%, about 94%, about 95%, about 96%, about 97%, about 98%, about 99%, or higher identity over a specified region, when compared and aligned for maximum correspondence over a comparison window or designated region) as measured using a BLAST or BLAST 2.0 sequence comparison algorithms with default parameters described below, or through manual alignment and also visual inspection (see e.g., the NCBI website http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described herein, the algorithms can account for gaps, and the like. In various embodiments, identity exists over a region that is at least about 25 amino acids, about 50 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window" includes reference to a segment of any one of the number of contiguous positions as desired. In some embodiments the "comparison window" can be selected from the group consisting of from about 50 to about 200, or about 100 to about 150, or greater than 150, if so desired in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see e.g., *Current Protocols in Molecular Biology* (Ausubel et al., eds. 1995 supplement)).

An example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of various embodiments. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto. The expression vectors useful in various embodiments described herein can contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., PhoS, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier; Chu et al., 1981, *Gene* 13:197. Such techniques can be used to introduce one or more exogenous DNA moieties into suitable host cells. A transfection may be transient.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

An "antigen-binding protein" ("ABP") as used herein means any protein that binds a specified target antigen. In this specification, the specified target antigen is the apelin protein or fragment or region thereof "Antigen-binding protein" includes but is not limited to antibodies and binding parts thereof, such as immunologically functional fragments. Peptibodies are another example of antigen-binding proteins.

The term "immunologically functional fragment" (or simply "fragment") of an antibody or immunoglobulin chain (heavy or light chain) antigen-binding protein, as used herein, is a species of antigen-binding protein comprising a portion (regardless of how that portion is obtained or synthesized) of an antibody that lacks at least some of the amino acids present in a full-length chain but which is still capable of specifically binding to an antigen.

"Specific binding" should be understood to mean that the predominant antigen bound by the antigen-binding protein is, the full length apelin molecule (SEQ ID NOs: 3-6) or a fragment thereof (e.g. SEQ ID NO: 31 or 32). This does not necessarily preclude, however, binding of an antigen-binding protein to proteins other than apelin. In various embodiments, the binding to other proteins represents less than about 5%, less than about 10%, less than about 15%, less than about 20% or less than about 25% of the total protein bound.

Fragments of antigen-binding proteins are biologically active in that they bind to the target antigen and can compete with other antigen-binding proteins, including intact antibodies, for binding to a given epitope or antigen. In some embodiments, the fragments are neutralizing fragments. In some embodiments, the fragments can block or reduce the likelihood of the interaction between apelin and APJ. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen-binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')$_2$, Fv, domain antibodies and single-chain antibodies, and can be derived from any mammalian source, including but not limited to human, mouse, rat, camelid or rabbit. It is further contemplated that a functional portion of the antigen-binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen-binding protein can include nonprotein components.

Certain antigen-binding proteins described herein are antibodies or are derived from antibodies. In certain embodiments, the polypeptide structure of the antigen-binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen-binding protein comprises or consists of avimers (tightly binding peptide).

An "Fc" region comprises two heavy chain fragments comprising the $C_H1$ and $C_H2$ domains of an antibody. The two heavy chain fragments are held together by two or more disulfide bonds and by hydrophobic interactions of the $C_H3$ domains.

A "Fab fragment" comprises one light chain and the $C_H1$ and variable regions of one heavy chain. The heavy chain of a Fab molecule cannot form a disulfide bond with another heavy chain molecule.

A "Fab' fragment" comprises one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

A "bivalent antigen-binding protein" or "bivalent antibody" comprises two antigen-binding sites. In some instances, the two binding sites have the same antigen specificities. Bivalent antigen-binding proteins and bivalent antibodies can be bispecific as defined herein. A bivalent antibody other than a "multispecific" or "multifunctional" antibody, in certain embodiments, typically is understood to have each of its binding sites identical.

A "multispecific antigen-binding protein" or "multispecific antibody" is one that targets more than one antigen or epitope.

A "bispecific," "dual-specific," or "bifunctional" antigen-binding protein or antibody is a hybrid antigen-binding protein or antibody, respectively, having two different antigen-binding sites. Bispecific antigen-binding proteins and antibodies are a species of multispecific antigen-binding protein antibody and can be produced by a variety of methods including, but not limited to, fusion of hybridomas or linking of Fab' fragments. See e.g., Songsivilai and Lachmann, 1990, *Clin. Exp. Immunol.* 79:315-321; Kostelny et al., 1992, *J. Immunol.* 148:1547-1553. The two binding sites of a bispecific antigen-binding protein or antibody will bind to two different epitopes, which can reside on the same or different protein targets.

Each individual immunoglobulin chain is typically composed of several "immunoglobulin domains." These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as $C_H1$, $C_H2$ and $C_H3$. The antibodies that are provided can have any of these isotypes and subtypes "Antigen-binding region" means a protein, or a portion of a protein, that specifically binds a specified antigen (e.g., a paratope). For example, that portion of an antigen-binding protein that contains the amino acid residues that interact with an antigen and confer on the antigen-binding protein its specificity and affinity for the antigen is referred to as "antigen-binding region." An antigen-binding region typically includes one or more Complementary Binding Regions (CDRs). Certain antigen-binding regions also include one or more "framework" regions. A "CDR" is an amino acid sequence that contributes to antigen-binding specificity and affinity. "Framework" regions can aid in maintaining the proper conformation of the CDRs to promote binding between the antigen-binding region and an antigen. Structurally, framework regions can be located in antibodies between CDRs.

In certain aspects, recombinant antigen-binding proteins that bind apelin, are provided. In this context, a "recombinant antigen-binding protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen-binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen-binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" and one full-length "heavy" chain. The amino-terminal portion of each chain typically includes a variable region that typically is responsible for antigen recognition. The carboxy-terminal portion of each chain typically defines a constant region that can be responsible for effector function. The variable regions of each light/heavy chain pair typically form the antigen-binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, *J. Mol. Biol.*, 196:901-917 (1987); Chothia et al., *Nature*, 342:878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the "AbM" definition and the contact definition.

The Kabat definition is a standard for numbering the residues in an antibody and is typically used to identify CDR regions. See e.g., Johnson & Wu, *Nucleic Acids Res.*, 28:214-8 (2000). The Chothia definition is similar to the Kabat definition, but the Chothia definition takes into account positions of certain structural loop regions. See e.g., Chothia et al., *J. Mol. Biol.*, 196: 901-17 (1986); Chothia et al., *Nature*, 342: 877-83 (1989). The "AbM" definition uses an integrated suite of computer programs produced by Oxford Molecular Group that model antibody structure. See e.g., Martin et al., *Proc. Natl. Acad. Sci.* (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See e.g., MacCallum et al., *J. Mol. Biol.*, 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

Specificity of antibodies in various embodiments or fragments thereof, for apelin can be determined based on affinity and/or avidity. Affinity, represented by the equilibrium constant for the dissociation of an antigen with an antibody (Kd), measures the binding strength between an antigenic determinant and an antibody-binding site. Avidity is the measure of the strength of binding between an antibody with its antigen. Avidity is related to both the affinity between an epitope with its antigen-binding site on the antibody, and the valence of the antibody, which refers to the number of antigen-binding sites specific for a particular epitope. The lesser the value of the Kd, the stronger the binding strength between an antigenic determinant and the antibody binding site.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See e.g., Songsivilai et al., *Clin. Exp. Immunol.*, 79:315-321 (1990); Kostelny et al., *J. Immunol.*, 148:1547-1553 (1992).

Some species of mammals can also produce antibodies having only a single heavy chain.

Each individual immunoglobulin chain is typically composed of several "immunoglobulin domains." These domains are the basic units of which antibody polypeptides are composed. The heavy chain C region typically comprises one or more domains that can be responsible for effector function. The number of heavy chain constant region domains will depend on the isotype. The antibodies that are provided can have any of isotypes and subtypes.

The term "variable region" or "variable domain" refers to a portion of the light and/or heavy chains of an antibody. In certain embodiments, variable regions of different antibodies differ extensively in amino acid sequence even among antibodies of the same species. The variable region of an antibody typically determines specificity of a particular antibody for its target The term "neutralizing antigen-binding protein" or "neutralizing antibody" refers to an antigen-binding protein or antibody, respectively, that binds to a ligand and prevents or reduces the binding of the ligand to a binding partner. This can be done, for example, by directly blocking a binding site on the ligand or by binding to the ligand and altering the ligand's ability to bind through indirect means (such as structural or energetic alterations in the ligand). In some embodiments, the term can also denote an antigen-binding protein that prevents the protein to which it is bound from performing a biological function. In assessing the binding and/or specificity of an antigen-binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, about 20-30%, about 30-40%, about 40-50%, about 50-60%, about 60-70%, about 70-80%, about 80-85%, about 85-90%, about 90-95%, about 95-97%, about 97-98%, about 98-99% or more (as measured in an in vitro competitive binding assay). In some embodiments, in the case of apelin antigen-binding proteins, such a neutralizing molecule can diminish the ability of apelin to bind the APJ. In some embodiments, the neutralizing ability is characterized and/or described via a competition assay. In some embodiments, the neutralizing ability is described in terms of an $IC_{50}$ or $EC_{50}$ value. In some embodiments, the antigen-binding proteins may be non-neutralizing antigen-binding proteins.

The term "target" refers to a molecule or a portion of a molecule capable of being bound by an antigen-binding protein. In certain embodiments, a target can have one or more epitopes. In certain embodiments, a target is an antigen. The use of "antigen" in the phrase "antigen-binding protein" simply denotes that the protein sequence that comprises the antigen can be bound by an antibody. In this context, it does not require that the protein be foreign or that it be capable of inducing an immune response.

The term "compete" when used in the context of antigen-binding proteins (e.g., neutralizing antigen-binding proteins or neutralizing antibodies) that compete for the same epitope means competition between antigen-binding proteins as determined by an assay in which the antigen-binding protein (e.g., antibody or immunologically functional fragment thereof) being tested prevents or inhibits (e.g., reduces) specific binding of a reference antigen-binding protein (e.g., a ligand, or a reference antibody) to a common antigen (e.g., apelin or a fragment thereof). Numerous types of competitive binding assays can be used to determine if one antigen-binding protein competes with another, for example: solid phase direct or indirect radioimmunoassay (RIA), solid phase direct or indirect enzyme immunoassay (EIA), sandwich competition assay (see e.g., Stahli et al., 1983, *Methods in Enzymology* 9:242-253); solid phase direct biotin-avidin EIA (see e.g., Kirkland et al., 1986, *J. Immunol.* 137:3614-3619) solid phase direct labeled assay, solid phase direct labeled sandwich assay (see e.g., Harlow and Lane, 1988, *Antibodies, A Laboratory Manual*, Cold Spring Harbor Press); solid phase direct label RIA using 1-125 label (see e.g., Morel et al., 1988, *Molec. Immunol.* 25:7-15); solid phase direct biotin-avidin EIA (see e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabelled test antigen-binding protein and a labeled reference antigen-binding protein. Competitive inhibition is measured by determining the amount of label bound to the solid surface or cells in the presence of the test antigen-binding protein. Usually the test antigen-binding protein is present in excess. Antigen-binding proteins identified by competition assay (competing antigen-binding proteins) include antigen-binding proteins binding to the same epitope as the reference antigen-binding proteins and antigen-binding proteins binding to an adjacent epitope sufficiently proximal to the epitope bound by the reference antigen-binding protein for steric hindrance to occur. Additional details regarding methods for determining competitive binding are provided in the examples herein. Usually, when a competing antigen-binding protein is present in excess, it will inhibit (e.g., reduce) specific binding of a reference antigen-binding protein to a common antigen by at least about 40-45%, about 45-50%, about about 50-55%, about 55-60%, about 60-65%, about 65-70%, about 70-75% or about 75% or more. In some instances, binding is inhibited by at least about 80-85%, about 85-90%, about 90-95%, about 95-97%, or about 97% or more.

The term "antigen" refers to a molecule or a portion of a molecule capable of being bound by a selective binding agent, such as an antigen-binding protein (including, e.g., an antibody or immunological functional fragment thereof). In some embodiments, the antigen is capable of being used in an animal to produce antibodies capable of binding to that antigen. An antigen can possess one or more epitopes that are capable of interacting with different antigen-binding proteins, e.g., antibodies.

The term "epitope" includes any determinant capable being bound by an antigen-binding protein, such as an antibody or to a T-cell receptor. An epitope is a region of an antigen that is bound by an antigen-binding protein that targets that antigen, and when the antigen is a protein, includes specific amino acids that directly contact the antigen-binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least about 50% (on a molar basis) of all macromolecular species present. In other embodiments, a substantially pure composition will comprise at least about 80%, about 85%, about 90%, about 95%, or about 99% of all macromolecular species present in the composition. In other embodiments, the object species is purified to essential homogeneity wherein contaminating species cannot be detected in the composition by conventional detection methods and thus the composition consists of a single detectable macromolecular species.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The terms "therapeutically effective amount" and "therapeutically effective dose" refer to the amount of an apelin antigen-binding protein determined to produce a therapeutic response in a mammal Such therapeutically effective amounts can be ascertained by one of ordinary skill in the art. The exact dose and formulation will depend on the purpose of the treatment, and will be ascertainable by one skilled in the art using known techniques (see e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy,* 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antigen-binding fragments, antibodies, peptibodies, carbohydrates or small organic molecules. An antibody can be made against apelin. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the specification. See e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Antigen-binding proteins (ABPs) that bind apelin, are provided herein. In some embodiments, the antigen-binding proteins provided are polypeptides which comprise one or more complementary determining regions (CDRs), as described herein. In some antigen-binding proteins, the CDRs are embedded into a "framework" region, which orients the CDR(s) such that the proper antigen-binding properties of the CDR(s) is achieved. In some embodiments, antigen-binding proteins provided herein can interfere with, block, reduce or modulate the interaction between apelin and APJ. Such antigen-binding proteins are denoted as "neutralizing." In some embodiments, the neutralizing antigen-binding protein binds to apelin in a location and/or manner that prevents apelin from binding to APJ.

In some embodiments, the antigen-binding proteins provided herein are capable of inhibiting apelin-mediated activity (including binding). In some embodiments, antigen-binding proteins binding to an apelin epitope can inhibit, inter alia, interactions between apelin and APJ and other physiological effects mediated by the apelin/APJ interaction. In some embodiments, the antigen-binding proteins are chimeras, such as a human/mouse chimera.

In some embodiments, the antigen-binding protein can bind to the mature form of apelin. In other embodiments the antigen-binding protein can bind in the prodomain of apelin.

The antigen-binding proteins that are disclosed herein have a variety of utilities. Some of the antigen-binding proteins, for instance, are useful in specific binding assays or for affinity purification of apelin, Some of the antigen-binding proteins may be useful for inhibiting binding of apelin to APJ, or inhibiting apelin/APJ-mediated activities. In some embodiments, binding of and antigen-binding protein to apelin can prevent angiogenesis. If angiogenesis is prevented this may treat retinopathy or cancer.

The antigen-binding proteins can be used in a variety of therapeutic applications, as explained herein. For example, in some embodiments the apelin antigen-binding proteins are useful for treating diseases and conditions associated with apelin and/or APJ such as diabetic retinopathy, cancer, or other pathologic disorder associated with angiogenesis.

In some embodiments, the antigen-binding proteins that are provided comprise one or more CDRs (e.g., 1, 2, 3, 4, 5 or 6 CDRs). In some embodiments, the antigen-binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature.

In certain embodiments, the polypeptide structure of the antigen-binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen-binding protein is an immunological fragment of an antibody (e.g., a Fab fragment, a Fab' fragment, a F(ab')$_2$ fragment, an Fv fragment, a diabody, or a single chain antibody molecule, such as an scFv)

In embodiments where the antigen-binding protein is used for therapeutic applications, an antigen-binding protein can inhibit, interfere with or modulate one or more biological activities of apelin. In one embodiment, an antigen-binding protein binds specifically to human apelin and/or substantially inhibits binding of human apelin to APJ by at least about 20%-40%, about 40-60%, about 60-80%, about 80-85%, or more (for example, by measuring binding in an in vitro competitive binding assay).

Some of the antigen-binding proteins that are provided herein are antibodies. In some embodiments, the antigen-binding protein has a $K_d$ of less (binding more tightly) than about $10^{-7}$, about $10^{-8}$, about $10^{-9}$, about $10^{-10}$, about $10^{-11}$, about $10^{-12}$, about $10^{-13}$M. In some embodiments, the antigen-binding protein has an $IC_{50}$ for blocking the binding of apelin to APJ of less than about 1 μM, about 1000 nM to about 100 nM, about 100 nM to about 10 nM, about about 10 nM to about 1 nM, about 1000 pM to about 500 pM, about 500 pM to about 200 pM, less than about 200 pM, about 200 pM to about 150 pM, about 200 pM to about 100 pM, about 100 pM to about 10 pM, about 10 pM to about 1 pM.

In some embodiments, the antigen-binding proteins bind to a specific conformational state of apelin to prevent apelin from interacting with APJ. When apelin is prevented from interacting with APJ, this can prevent or block apelin or APJ mediated activity and the resultant pathology resulting from the apelin/APJ interaction.

As described herein, an antigen-binding protein to apelin can comprise a humanized antibody and/or part thereof. A practical application of such a strategy is the "humanization" of the mouse humoral immune system.

In certain embodiments, a humanized antibody is substantially non-immunogenic in humans. In certain embodiments, a humanized antibody has substantially the same affinity for a target as an antibody from another species from which the humanized antibody is derived. See e.g., U.S. Pat. No. 5,530,101, U.S. Pat. No. 5,693,761; U.S. Pat. No. 5,693,762; and U.S. Pat. No. 5,585,089.

In certain embodiments, amino acids of an antibody variable domain that can be modified without diminishing the native affinity of the antigen-binding domain while reducing its immunogenicity are identified. See e.g., U.S. Pat. Nos. 5,766,886 and 5,869,619.

In certain embodiments, modification of an antibody by methods known in the art is typically designed to achieve increased binding affinity for a target and/or to reduce immunogenicity of the antibody in the recipient. In certain embodiments, humanized antibodies can be modified to eliminate glycosylation sites in order to increase affinity of the antibody for its cognate antigen. See e.g., Co et al., Mol. Immunol., 30:1361-1367 (1993). In certain embodiments, techniques such as "reshaping," "hyperchimerization," or "veneering/resurfacing" are used to produce humanized antibodies. See e.g., Vaswami et al., *Annals of Allergy, Asthma, & Immunol.* 81:105 (1998); Roguska et al., *Prot. Engin.,* 9:895-904 (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al., *J. Immunol.,* 62(6):3663-71 (1999).

In certain instances, humanizing antibodies can result in a loss of antigen-binding capacity. The humanized antibodies can then be "back mutated." In such embodiments, the humanized antibody can be mutated to include one or more of the amino acid residues found in the donor antibody. See e.g., Saldanha et al., *Mol. Immunol.* 36:709-19 (1999).

In certain embodiments the complementarity determining regions (CDRs) of the light and heavy chain variable regions of an antibody to apelin can be grafted to framework regions (FRs) from the same, or another, species. In certain embodiments, the CDRs of the light and heavy chain variable regions of an antibody to apelin can be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to apelin heavy chain or light chain are replaced with the FRs from a different heavy chain or light chain. In certain embodiments, rare amino acids in the FRs of the heavy and light chains of an antibody to apelin are not replaced, while the rest of the FR amino acids are replaced. Rare amino acids are specific amino acids that are in positions in which they are not usually found in FRs. In certain embodiments, the grafted variable regions from an antibody to apelin can be used with a constant region that is different from the constant region of an antibody to apelin. In certain embodiments, the grafted variable regions are part of a single chain Fv antibody. CDR grafting is described, e.g., in U.S. Pat. Nos. 6,180,370, 6,054,297, 5,693,762, 5,859,205, 5,693,761, 5,565,332, 5,585,089, and 5,530,101, and in Jones et al., *Nature,* 321: 522-525 (1986); Riechmann et al., *Nature,* 332: 323-327 (1988); Verhoeyen et al., *Science,* 239:1534-1536 (1988), Winter, FEBS Letts., 430:92-94 (1998), which are hereby incorporated by reference for any purpose.

In certain embodiments, antigen-binding proteins (such as antibodies) are produced by immunization with an antigen (e.g., apelin or a fragment thereof). The antibodies can be produced by immunization with full-length apelin, a soluble form of apelin, the catalytic domain alone, the mature form of apelin, a splice variant form of apelin, or a fragment thereof. In certain embodiments, the antibodies of can be polyclonal or monoclonal, and/or can be recombinant antibodies In certain embodiments, strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In other embodiments, amino acids in the framework regions of the variable domains can be targeted. Such framework regions have been shown to contribute to the target binding properties of certain antibodies. See e.g., Hudson, *Curr. Opin. Biotech.,* 9:395-402 (1999) and references therein.

In certain embodiments, smaller and more effectively screened libraries of antibody variants can be produced by restricting random or site-directed mutagenesis to hyper-mutation sites in the CDRs, which are sites that correspond to areas prone to mutation during the somatic affinity maturation process. See e.g., Chowdhury & Pastan, Nature Biotech., 17: 568-572 (1999) and references therein. In certain embodiments, certain types of DNA elements can be used to identify hyper-mutation sites including, but not limited to, certain direct and inverted repeats, certain consensus sequences, certain secondary structures, and certain palindromes. For example, such DNA elements that can be used to identify hyper-mutation sites include, but are not limited to, a tetrabase sequence comprising a purine (A or G), followed by guanine (G), followed by a pyrimidine (C or T), followed by either adenosine or thymidine (A or T) (i.e., A/G-G-C/T-A/T). Another example of a DNA element that can be used to identify hyper-mutation sites is the serine codon, A-G-C/T.

For preparation of suitable antibodies for various embodiments e.g., recombinant, monoclonal, or polyclonal antibodies, many techniques known in the art can be used (see e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see e.g., Kuby, *Immunol.* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides for various embodiments. Also, transgenic mice, or other organisms such as other mammals, may be used to express humanized or human antibodies (see e.g., U.S. Pat. Nos. 5,545,807; 5,545,806; 5,569,825; 5,625,126; 5,633,425; 5,661,016; Marks et al., *Bio/Technology,* 10:779-783 (1992); Lonberg et al., *Nature,* 368:856-859 (1994); Morrison, *Nature,* 368: 812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see e.g., McCafferty et al., *Nature* 348:552-554 (1990); Marks et al., *Biotechnology* 10:779-783 (1992)). Antibodies can also be made bispecific, i.e., able to recognize two different antigens (see e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (e.g. a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg & Kay, U.S. Pat. Nos. 5,591,669 and 6,023,010 to Krimpenfort & Berns, U.S. Pat. Nos. 5,612,205, 5,721,367, and 5,789,215 to Berns et al., and U.S. Pat. No. 5,643,763 to Choi & Dunn, and GenPharm International U.S. patent application Ser. Nos. 07/574,748, 07/575,962, 07/810,279, 07/853,408, 07/904,068, 07/990,860, 08/053,131, 08/096,762, 08/155,301, 08/161,739, 08/165,699, 08/209,741, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference.

In one embodiment, the antibody is conjugated to an "effector" moiety. The effector moiety can be any number of molecules, including labeling moieties such as radioactive labels or fluorescent labels, or can be a therapeutic moiety.

The antibodies can be fused to additional amino acid residues. Such amino acid residues can be a peptide tag, perhaps to facilitate isolation. Other amino acid residues for homing of the antibodies to specific organs or tissues are also contemplated.

In certain embodiments the antibody or the antigen-binding region of any of the monoclonal antibodies described herein can be used to treat cancer or retinopathy.

"Cancer" should be understood to be a general term that can be used to indicate any of various types of malignant neoplasms, which may invade surrounding tissues, may metastasize to several sites and may likely recur after attempted removal. The term may also refer to any carcinoma or sarcoma.

"Retinopathy" should be understood to mean a non-inflammatory disease of the retina, as distinguished from retinitis. "Diabetic retinopathy" should be understood to mean retinal changes occurring in diabetes, that can be marked by punctuate hemorrhages, microaneurysms and sharply defined waxy exudates.

In treating cancer, the antigen-binding region can be joined to at least a functionally active portion of a second protein having therapeutic activity. The second protein can include, but is not limited to, an enzyme, lymphokine, oncostatin or toxin. Suitable toxins include doxorubicin, daunorubicin, taxol, ethiduim bromide, mitomycin, etoposide, tenoposide, vincristine, vinblastine, colchicine, dihydroxy anthracin dione, actinomycin D, diphtheria toxin, Pseudomonas exotoxin (PE) A, PE40, ricin, abrin, glucocorticoid and radioisotopes.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels of the antibody of interest.

In certain embodiments, antigen-binding proteins can comprise an immunoglobulin molecule of at least one of the IgG1, IgG2, IgG3, IgG4, Ig E, IgA, IgD, and IgM isotype. In certain embodiments, antigen-binding proteins comprise a human kappa light chain and/or a human heavy chain. In certain embodiments, the heavy chain is of the IgG1, IgG2, IgG3, IgG4, IgE, IgA, IgD, or IgM isotype. In certain embodiments, antigen-binding proteins have been cloned for expression in mammalian cells. In certain embodiments, antigen-binding proteins comprise a constant region other than any of the constant regions of the IgG1, IgG2, IgG3, IgG4, IgE, IgA, IgD, and IgM isotype.

In certain embodiments, substantial modifications in the functional and/or chemical characteristics of antibodies to apelin can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a nonnative residue such that there is little or no effect on the polarity or charge of the amino acid residue at that position. Furthermore, any native residue in the polypeptide can also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of antibodies to apelin, or to increase or decrease the affinity of the antibodies to apelin as described herein.

In certain embodiments, antibodies or antigen-binding proteins can be expressed in cell lines other than hybridoma cell lines. Sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and produce antibodies with constitutive HGF binding properties. Appropriate expression vectors for mammalian host cells are well known.

In certain embodiments, antigen-binding proteins comprise one or more polypeptides. Any of a variety of expression vector/host systems can be utilized to express polynucleotide molecules encoding polypeptides comprising one or more antigen-binding protein components or the antigen-binding protein itself. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide comprising one or more antigen-binding protein components or the antigen-binding protein itself is recombinantly expressed in yeast. Certain such embodiments use commercially available expression systems, e.g., the *Pichia* Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide comprising one or more antigen-binding protein components or the antigen-binding protein itself is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide comprising one or more antigen-binding protein components or the antigen-binding protein itself is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide comprising one or more antigen-binding protein components or the antigen-binding protein itself is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia* larvae. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S. frugiperda* cells or *Trichoplusia* larvae. See e.g., Smith et al., *J. Virol.*, 46: 584 (1983); Engelhard et al., *Proc. Nat. Acad. Sci.* (USA), 91: 3224-7 (1994).

In certain embodiments, polypeptides comprising one or more antigen-binding protein components or the antigen-binding protein itself made in bacterial cells are produced as insoluble inclusion bodies in the bacteria. Host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In certain embodiments, the lysate is cleared by sonication, and cell debris is pelleted by centrifugation for 10 minutes at 12,000×g. In certain embodiments, the polypeptide-containing pellet is resuspended in 50 mM Tris, pH 8, and 10 mM EDTA; layered over 50% glycerol; and centrifuged for 30 minutes at 6000×g. In certain embodiments, that pellet can be resuspended in standard phosphate buffered saline solution (PBS) free of $Mg^{++}$ and $Ca^{++}$. In certain embodiments, the polypeptide is further purified by fractionating the resuspended pellet in a denaturing SDS polyacrylamide gel (see e.g., Sambrook et al., supra). In certain embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides, e.g., polypeptides comprising one or more antigen-binding protein components or the antigen-binding protein itself. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a co-solvent is used to increase the efficiency of refolding. Exemplary cosolvents include, but are not limited to, glycerol, polyethylene glycol of various molecular weights, and arginine.

In certain embodiments, one substantially purifies a polypeptide comprising one or more antigen-binding protein components or the antigen-binding protein itself. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high pressure liquid chromatography (HPLC). In certain embodiments, purification steps can be changed or certain steps can be omitted, and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide comprising one or more antigen-binding protein components or the antigen-binding protein itself is partially purified. Partial purification can be accomplished by using fewer purification steps or by utilizing different forms of the same general purification scheme. For example, in certain embodiments, cation-exchange column chromatography performed utilizing an HPLC apparatus will generally result in a greater "fold purification" than the same technique utilizing a low-pressure chromatography system. In certain embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See e.g., Capaldi et al., Biochem. *Biophys. Res. Comm.*, 76: 425 (1977). It will be appreciated that under different electrophoresis conditions, the apparent molecular weights of purified or partially purified polypeptide can be different.

In various embodiments described herein, antibodies can be used in vivo and in vitro for investigative or diagnostic methods, which are well known in the art. The diagnostic methods include kits, which contain antibodies in various embodiments. In other embodiments the antibodies described herein can be used as a therapeutic.

It is understood that the anti-apelin antibodies, where used in a mammal for the purpose of prophylaxis or treatment, can be administered in the form of a composition that additionally can comprise a pharmaceutically acceptable carrier. Suitable pharmaceutically acceptable carriers include, for example, one or more of water, saline, phosphate buffered saline, dextrose, glycerol, ethanol and the like, as well as combinations thereof.

Pharmaceutically acceptable carriers can further comprise minor amounts of auxiliary substances such as wetting or emulsifying agents, preservatives or buffers, which enhance the shelf life or effectiveness of the antigen-binding proteins. The compositions of the injection can, as is well known in the art, be formulated so as to provide quick, sustained or delayed release of the active ingredient after administration to the mammal.

Pharmaceutical formulations, particularly, of the antibodies for use described herein can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g., Zn-protein complexes); and/or non-ionic surfactants. The antibody can be formulated at a concentration of between 0.5-200 mg/ml.

In therapeutic applications, compositions are administered to a patient suffering from a disease (e.g., diabetic retinopathy) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" as referred to herein can include both humans and other animals, particularly mammals. Thus the methods are applicable to both human therapy and veterinary applications. In various embodiments the patient is a mammal. The mammal can be a primate, or even a human.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired antigen-binding protein to apelin, with or without additional therapeutic agents, in a pharmaceutically acceptable vehicle. In certain embodiments, a vehicle for parenteral injection is sterile distilled water in which an antigen-binding protein to apelin, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, methods are provided for inhibiting angiogenesis or tumorigenesis and are used to treat a patient with disease or condition that involves angiogenesis or tumorigenesis. As used herein, the phrase "disease or condition involving angiogenesis" is intended to include, but is not limited to, hemangioma, solid tumors, leukemias, lymphomas, myelomas, plaque neovascularization, corneal diseases, rubeosis, neovascular glaucoma, retinopathy, exudative age-related macular degeneration (AMD), proliferative diabetic retinopathy (PDR), diabetic macular edema (DME), neovascular glaucoma, corneal neovascularization (trachoma), and pterygium, diabetic retinopathy, retrolental fibroplasia, diabetic neovascularization, macular degeneration, uterine bleeding, endometrial hyperplasia and carcinoma, endometriosis, myometrial fibroids (uterine leiomyomas) and adenomyosis, ovarian hyperstimulation syndrome, tumorigenesis or cancer.

Other aspects of the invention will be appreciated by one skilled in the art, and are described herein. Although various embodiments of the invention have been described herein, including the following examples, those skilled in the art will readily appreciate that the specific examples and studies detailed herein are only illustrative. It should be understood that various modifications can be made without departing from the spirit of the invention.

EXAMPLES

Example 1

Antibody Generation

Mice were immunized with an apelin peptide (QRPRLSHKGPMPF) (SEQ ID NO: 31) conjugated with KLH and then boosted for 10 times. Hybridomas were then prepared from which monoclonal antibodies could be obtained.

Hybridomas were screened using an ELISA-based assay to identify positive binders. The monoclonal antibody, antibody A (Ab A), was selected and purified for further characterization of affinity binding and neutralizing activity.

The amino acid sequence of the antibody is shown in FIG. 1. The figure presents the sequence of the light chain and heavy chain of Ab A to apelin. The CDR regions in the heavy and light chain are shown in bold, italic type. The signal sequences are underlined. Additionally, the individual CDR's are presented.

Example 2

Epitope Mapping

The antibody binding site was mapped using an ELISA-based assay. Briefly, various biotinylated apelin peptides (SEQ ID NOs: 7-22) were captured onto neutravidin coated plates and incubated with apelin antibody. Bound antibody was detected with horseradish peroxidase-conjugated goat anti-mouse Fc in the presence of the chromogenic substrate. The absorbance was read at 650 nm. The Ab A was determined to bind to the epitope comprising amino acids PRLSHKG (SEQ ID NO: 32) of apelin as shown in FIG. 2. Ab A is believed to neutralize all active forms of apelin.

Example 3

Binding Affinity of Ab A

Binding affinity of Ab A was determined using BIAcore solution equilibrium binding analysis. The results are shown in Table 2 and FIG. 3. Briefly, biotin-labeled apelin was immobilized at high density on a neutravidin surface. Ab A was incubated with apelin 12 at RT for over 4 hours before injected over the immobilized surfaces. The dissociation equilibrium constant ($K_d$) was obtained from a nonlinear regression analysis of the competition curve using a one-site homogeneous binding model (KinExATM Pro software). The $K_d$ value was estimated to be 6 nM.

TABLE 2

| Antibody | $K_D$ (nM) | 95% confidence interval (nM) |
| --- | --- | --- |
| Ab A | 6 | 4-7 |

Example 4

Neutralization Activity of Ab A

CHOK1 cells overexpressing the human apelin receptor/APJ were used to measure apelin-induced changes in cAMP levels. Cells were plated the night before the assay at a density of $2 \times 10^4$ cells/well in a 96-well assay plate. Serial dilutions of Ab A (10-6 M-10-9 M) were incubated with 6 nM of apelin (Phoenix Pharmaceuticals, Inc.) for 20 min before being added to 500 nM of forskolin and the cells. The cAMP level was measured using HTRF assay kit according to the manufacture's protocol (Cisbio). The luminescence was measured using RUBY star plate reader (BMG LABTECH). The neutralizing activity of Ab A ($IC_{50}$) was calculated from the value of peak luminescence. The result indicated that Ab A dose-dependently inhibited apelin-mediated changes in cAMP levels, with $IC_{50}$ about 18 nM.

Example 5

Anti-Angiogenesis Activity of Ab A

Figure 4A:
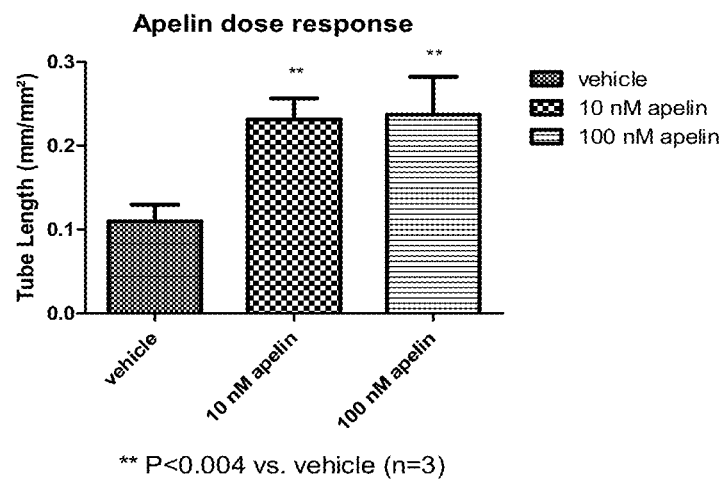
FIGS. 4A-B. These figures present results of an anti-angiogenesis experiment.
Figure 4B:
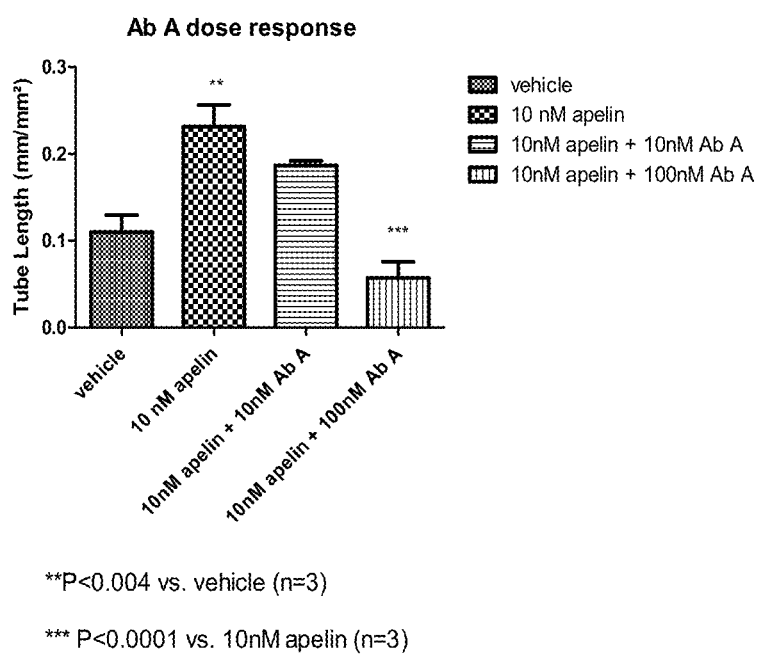

Angiogenesis activity was measured using Cellplayer GFP AngioKit-96 (Essen Bioscience). Briefly, human endothelial cells were co-cultured with other human cells in a specially designed medium and treated with apelin with or without Ab A for three days. The endothelial cells proliferated and migrated to form threadlike tubule structures. The tube formation, which is a morphogenic indicator of angiogenesis was measured using IncuCyte angiogenesis module (Essen Bioscience). Apelin stimulated the tube formation and Ab A inhibited the apelin-induced tube formation as clearly indicated by decreased tube formation shown in FIG. 4B.

Example 6

Treatment of Diabetic Retinopathy

A subject in need of treatment for diabetic retinopathy will be injected intravitreal with an antibody prepared against apelin that is known to affect angiogenesis, e.g. Ab A. The treatment will continue until there is an improvement in the condition as indicated by a decrease in neovascularization. Such an improvement can also be determined by measurement of either biochemical or physiological parameters deemed appropriate by one of skill in the art. For example, see Tao et al., Invest Opthamol Visual Sci., 51:4237-4242 (2010).

Example 7

Systemic Administration of Apelin Ab on Retinal Neovascularization

Figure 6:
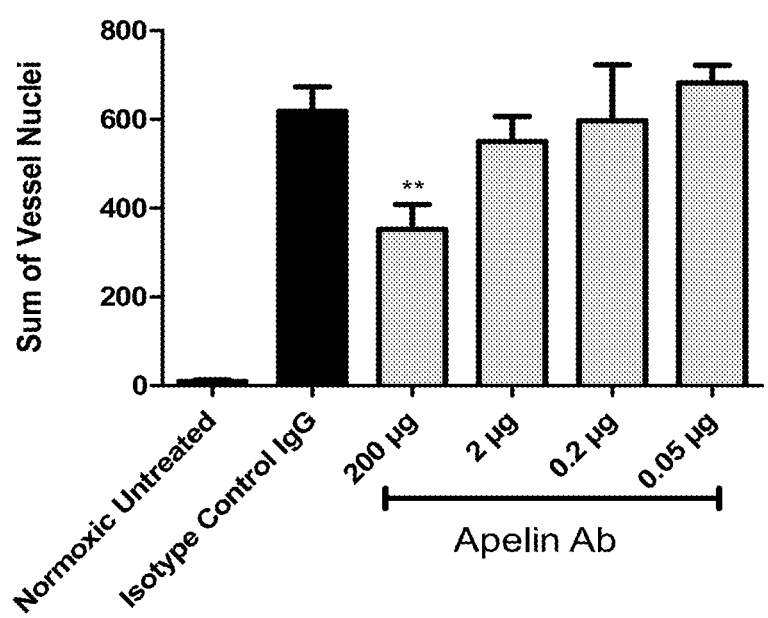
FIG. 6. This figure demonstrates the effects of systemic administration of apelin antibody on retinal neovascularization.

OIR (oxygen-induced retinopathy) animal model was used to examine the effects of apelin Ab on retinal neovascularization. The IgG isotype control (200 ug) or apelin Ab (200 ug, 2 ug, 0.2 ug and 0.05 ug) was administered s.c. daily for 9 days starting on P8 (8 days post-natal). On P17, mice were sacrificed and eyes were enucleated. Ten sections of each eye from each group were stained with hematoxylin-eosin (HE) and the nuclei extending beyond the internal limiting membrane were counted. Apelin Ab (200 ug) significantly inhibited the retinal neovascularization. (FIG. 6)

Example 8

Intravitreal Injection of Apelin Ab on Retinal Neovascularization

Figure 7:
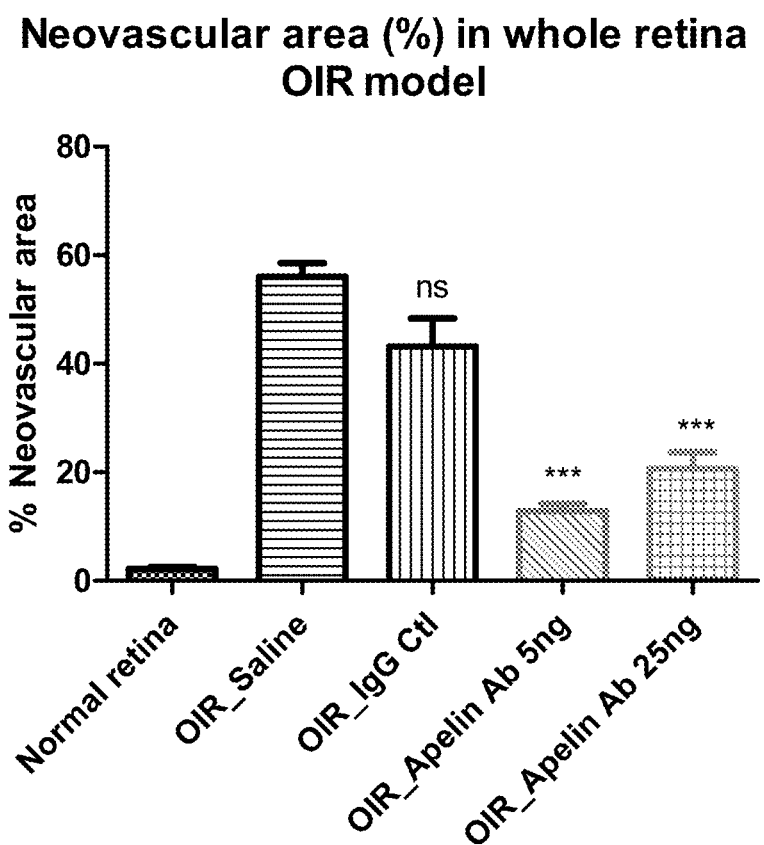
FIG. 7. This figure demonstrates the effect of intravitreal injection of apelin antibody on retinal neovascularization.

Following the induction of OIR by oxygen cycling, eyes of P12 mice were treated with an intravitreal injection of saline, IgG control or apelin Ab (5 and 25 ng). On P17, retinal flatmounts were stained with fluorescent-labeled isolectin B4 and retinal vascular growth was assessed. Apelin Ab significantly reduced the neovascular area in retina. (FIG. 7)

Throughout this specification various publications, patents and patent applications have been referenced. The disclosures of these documents in their entireties are hereby incorporated by reference into this application. The reference to such documents, however, should not be construed as an acknowledgment that such documents are prior art to the application. Further, merely because a document may be incorporated by reference, this does not necessarily indicate that the applicants are in complete agreement with the document's contents.

What is claimed:

1. A method for inhibiting retinal neovascularization in a patient in need thereof comprising administering to the patient a therapeutically effective amount of a monoclonal antibody or fragment thereof, wherein the monoclonal antibody or fragment thereof specifically binds to human apelin at an epitope with the sequence of SEQ ID NO: 32 and inhibits the binding of human apelin to the APJ receptor.

2. The method of claim 1, wherein the monoclonal antibody or fragment thereof comprises light chain complementarity determining regions L1, L2, and L3 and heavy chain complementarity determining regions H1, H2, and H3, wherein L1, L2, and L3 have the amino acid sequence of SEQ ID NO: 23, SEQ ID NO: 24, and SEQ ID NO: 25, respectively, and wherein H1, H2, and H3 have the amino acid sequence of SEQ ID NO: 28, SEQ ID NO: 29, and SEQ ID NO: 30, respectively.

3. The method of claim 1, wherein the monoclonal antibody or fragment thereof comprises a light chain comprising the sequence of SEQ ID NO: 2 and a heavy chain comprising the sequence of SEQ ID NO: 27.

4. The method of claim 1, wherein the monoclonal antibody is a humanized antibody, a chimeric antibody, or a multispecific antibody.

5. The method of claim 1, wherein the patient has retinopathy.

6. The method of claim 5, wherein the retinopathy is diabetic retinopathy.

7. The method of claim 1, wherein the patient has exudative age-related macular degeneration.

8. The method of claim 1, wherein the monoclonal antibody or fragment thereof is administered to the patient parenterally.

9. The method of claim 1, wherein the monoclonal antibody or fragment thereof is administered to the patient subcutaneously.

10. The method of claim 1, wherein the monoclonal antibody or fragment thereof is administered to the patient intravitreally.

11. A method for treating retinopathy in a patient in need thereof comprising administering to the patient a therapeutically effective amount of a monoclonal antibody or fragment thereof, wherein the monoclonal antibody or fragment thereof specifically binds to human apelin at an epitope with the sequence of SEQ ID NO: 32 and inhibits the binding of human apelin to the APJ receptor.

12. The method of claim 11, wherein the monoclonal antibody or fragment thereof comprises light chain complementarity determining regions L1, L2, and L3 and heavy chain complementarity determining regions H1, H2, and H3, wherein L1, L2, and L3 have the amino acid sequence of SEQ ID NO: 23, SEQ ID NO: 24, and SEQ ID NO: 25, respectively, and wherein H1, H2, and H3 have the amino acid sequence of SEQ ID NO: 28, SEQ ID NO: 29, and SEQ ID NO: 30, respectively.

13. The method of claim 11, wherein the monoclonal antibody or fragment thereof comprises a light chain comprising the sequence of SEQ ID NO: 2 and a heavy chain comprising the sequence of SEQ ID NO: 27.

14. The method of claim 11, wherein the monoclonal antibody is a humanized antibody, a chimeric antibody, or a multispecific antibody.

15. The method of claim 11, wherein the monoclonal antibody or fragment thereof is administered to the patient parenterally.

16. The method of claim 11, wherein the monoclonal antibody or fragment thereof is administered to the patient subcutaneously.

17. The method of claim 11, wherein the monoclonal antibody or fragment thereof is administered to the patient intravitreally.

18. The method of claim 11, wherein the retinopathy is diabetic retinopathy.

19. The method of claim 18, wherein the diabetic retinopathy is proliferative diabetic retinopathy.

\* \* \* \* \*

```
SEQUENCE LISTING

<160> NUMBER OF SEQ ID NOS: 32

<210> SEQ ID NO 1
<211> LENGTH: 133
<212> TYPE: PRT
<213> ORGANISM: Artificial Sequence
<220> FEATURE:
<223> OTHER INFORMATION: Antibody light chain

<400> SEQUENCE: 1

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asp Ser Arg Thr Arg Lys Asn Tyr Leu Ala Trp Tyr Gln Gln
    50                  55                  60

Lys Pro Gly Gln Ser Pro Lys Leu Leu Ile Ser Trp Ala Ser Ile Arg
65                  70                  75                  80

Glu Ser Gly Val Pro Asp Arg Phe Thr Gly Ser Gly Ser Gly Thr Asp
                85                  90                  95

Phe Thr Leu Ser Ile Ser Ser Val Gln Ala Glu Asp Leu Ala Val Tyr
            100                 105                 110

Tyr Cys Lys Gln Ser Tyr Tyr Leu Leu Thr Phe Gly Ala Gly Thr Lys
        115                 120                 125

Leu Glu Leu Lys Arg
    130

<210> SEQ ID NO 2
```

```
<211> LENGTH: 113
<212> TYPE: PRT
<213> ORGANISM: Artificial Sequence
<220> FEATURE:
<223> OTHER INFORMATION: Antibody light chain

<400> SEQUENCE: 2

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asp Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Ser Trp Ala Ser Ile Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Gln Ala Glu Asp Leu Ala Val Tyr Tyr Cys Lys Gln
                85                  90                  95

Ser Tyr Tyr Leu Leu Thr Phe Gly Ala Gly Thr Lys Leu Glu Leu Lys
            100                 105                 110

Arg

<210> SEQ ID NO 3
<211> LENGTH: 77
<212> TYPE: PRT
<213> ORGANISM: Homo sapiens

<400> SEQUENCE: 3

Met Asn Leu Arg Leu Cys Val Gln Ala Leu Leu Leu Trp Leu Ser
1               5                   10                  15

Leu Thr Ala Val Cys Gly Gly Ser Leu Met Pro Leu Pro Asp Gly Asn
            20                  25                  30

Gly Leu Glu Asp Gly Asn Val Arg His Leu Val Gln Pro Arg Gly Ser
        35                  40                  45

Arg Asn Gly Pro Gly Pro Trp Gln Gly Arg Arg Lys Phe Arg Arg
    50                  55                  60

Gln Arg Pro Arg Leu Ser His Lys Gly Pro Met Pro Phe
65                  70                  75

<210> SEQ ID NO 4
<211> LENGTH: 77
<212> TYPE: PRT
<213> ORGANISM: Mus musculus

<400> SEQUENCE: 4

Met Asn Leu Arg Leu Cys Val Gln Ala Leu Leu Leu Trp Leu Ser
1               5                   10                  15

Leu Thr Ala Val Cys Gly Val Pro Leu Met Leu Pro Asp Gly Thr
            20                  25                  30

Gly Leu Glu Glu Gly Ser Met Arg Tyr Leu Val Lys Pro Arg Thr Ser
        35                  40                  45

Arg Thr Gly Pro Gly Ala Trp Gln Gly Gly Arg Arg Lys Phe Arg Arg
    50                  55                  60

Gln Arg Pro Arg Leu Ser His Lys Gly Pro Met Pro Phe
65                  70                  75

<210> SEQ ID NO 5
```

```
<211> LENGTH: 77
<212> TYPE: PRT
<213> ORGANISM: Rattus rattus

<400> SEQUENCE: 5

Met Asn Leu Ser Phe Cys Val Gln Ala Leu Leu Leu Trp Leu Ser
1               5                  10                  15

Leu Thr Ala Val Cys Gly Val Pro Leu Met Leu Pro Asp Gly Lys
                20                  25                  30

Gly Leu Glu Glu Gly Asn Met Arg Tyr Leu Val Lys Pro Arg Thr Ser
            35                  40                  45

Arg Thr Gly Pro Gly Ala Trp Gln Gly Arg Arg Lys Phe Arg Arg
        50                  55                  60

Gln Arg Pro Arg Leu Ser His Lys Gly Pro Met Pro Phe
65                  70                  75

<210> SEQ ID NO 6
<211> LENGTH: 77
<212> TYPE: PRT
<213> ORGANISM: Bos taurus

<400> SEQUENCE: 6

Met Asn Leu Arg Arg Cys Val Gln Ala Leu Leu Leu Trp Leu Cys
1               5                  10                  15

Leu Ser Ala Val Cys Gly Gly Pro Leu Leu Gln Thr Ser Asp Gly Lys
                20                  25                  30

Glu Met Glu Glu Gly Thr Ile Arg Tyr Leu Val Gln Pro Arg Gly Pro
            35                  40                  45

Arg Ser Gly Pro Gly Pro Trp Gln Gly Gly Arg Arg Lys Phe Arg Arg
        50                  55                  60

Gln Arg Pro Arg Leu Ser His Lys Gly Pro Met Pro Phe
65                  70                  75

<210> SEQ ID NO 7
<211> LENGTH: 13
<212> TYPE: PRT
<213> ORGANISM: Homo sapiens

<400> SEQUENCE: 7

Gln Arg Pro Arg Leu Ser His Lys Gly Pro Met Pro Phe
1               5                  10

<210> SEQ ID NO 8
<211> LENGTH: 13
<212> TYPE: PRT
<213> ORGANISM: Homo sapiens

<400> SEQUENCE: 8

Gln Arg Pro Arg Leu Ser His Lys Gly Pro Met Pro Phe
1               5                  10

<210> SEQ ID NO 9
<211> LENGTH: 13
<212> TYPE: PRT
<213> ORGANISM: Homo sapiens

<400> SEQUENCE: 9

Glu Arg Pro Arg Leu Ser His Lys Gly Pro Met Pro Phe
1               5                  10

<210> SEQ ID NO 10
```

```
<211> LENGTH: 13
<212> TYPE: PRT
<213> ORGANISM: Homo sapiens

<400> SEQUENCE: 10

Gln Arg Pro Arg Leu Ser His Lys Gly Pro Met Pro Ala
1               5                   10

<210> SEQ ID NO 11
<211> LENGTH: 13
<212> TYPE: PRT
<213> ORGANISM: Homo sapiens

<400> SEQUENCE: 11

Gln Arg Pro Arg Leu Ser His Lys Gly Pro Met Pro Phe
1               5                   10

<210> SEQ ID NO 12
<211> LENGTH: 11
<212> TYPE: PRT
<213> ORGANISM: Homo sapiens

<400> SEQUENCE: 12

Pro Arg Leu Ser His Lys Gly Pro Met Pro Phe
1               5                   10

<210> SEQ ID NO 13
<211> LENGTH: 10
<212> TYPE: PRT
<213> ORGANISM: Homo sapiens

<400> SEQUENCE: 13

Arg Leu Ser His Lys Gly Pro Met Pro Phe
1               5                   10

<210> SEQ ID NO 14
<211> LENGTH: 9
<212> TYPE: PRT
<213> ORGANISM: Homo sapiens

<400> SEQUENCE: 14

Leu Ser His Lys Gly Pro Met Pro Phe
1               5

<210> SEQ ID NO 15
<211> LENGTH: 8
<212> TYPE: PRT
<213> ORGANISM: Homo sapiens

<400> SEQUENCE: 15

Ser His Lys Gly Pro Met Pro Phe
1               5

<210> SEQ ID NO 16
<211> LENGTH: 7
<212> TYPE: PRT
<213> ORGANISM: Homo sapiens

<400> SEQUENCE: 16

His Lys Gly Pro Met Pro Phe
1               5

<210> SEQ ID NO 17
<211> LENGTH: 11
<212> TYPE: PRT
```

```
<213> ORGANISM: Homo sapiens

<400> SEQUENCE: 17

Arg Pro Arg Leu Ser His Lys Gly Pro Met Pro
1               5                   10

<210> SEQ ID NO 18
<211> LENGTH: 10
<212> TYPE: PRT
<213> ORGANISM: Homo sapiens

<400> SEQUENCE: 18

Arg Pro Arg Leu Ser His Lys Gly Pro Met
1               5                   10

<210> SEQ ID NO 19
<211> LENGTH: 9
<212> TYPE: PRT
<213> ORGANISM: Homo sapiens

<400> SEQUENCE: 19

Arg Pro Arg Leu Ser His Lys Gly Pro
1               5

<210> SEQ ID NO 20
<211> LENGTH: 8
<212> TYPE: PRT
<213> ORGANISM: Homo sapiens

<400> SEQUENCE: 20

Arg Pro Arg Leu Ser His Lys Gly
1               5

<210> SEQ ID NO 21
<211> LENGTH: 7
<212> TYPE: PRT
<213> ORGANISM: Homo sapiens

<400> SEQUENCE: 21

Arg Pro Arg Leu Ser His Lys
1               5

<210> SEQ ID NO 22
<211> LENGTH: 14
<212> TYPE: PRT
<213> ORGANISM: Homo sapiens

<400> SEQUENCE: 22

Gly Pro Gly Ala Trp Gln Gly Gly Arg Arg Lys Phe Arg Arg
1               5                   10

<210> SEQ ID NO 23
<211> LENGTH: 16
<212> TYPE: PRT
<213> ORGANISM: Artificial Sequence
<220> FEATURE:
<223> OTHER INFORMATION: CDR region

<400> SEQUENCE: 23

Lys Ser Ser Gln Ser Leu Leu Asp Ser Arg Thr Arg Lys Asn Tyr Leu
1               5                   10                  15

<210> SEQ ID NO 24
<211> LENGTH: 7
<212> TYPE: PRT
```

```
<213> ORGANISM: Artificial Sequence
<220> FEATURE:
<223> OTHER INFORMATION: CDR region

<400> SEQUENCE: 24

Trp Ala Ser Ile Arg Glu Ser
1               5

<210> SEQ ID NO 25
<211> LENGTH: 8
<212> TYPE: PRT
<213> ORGANISM: Artificial Sequence
<220> FEATURE:
<223> OTHER INFORMATION: CDR region

<400> SEQUENCE: 25

Lys Gln Ser Tyr Tyr Leu Leu Thr
1               5

<210> SEQ ID NO 26
<211> LENGTH: 138
<212> TYPE: PRT
<213> ORGANISM: Artificial Sequence
<220> FEATURE:
<223> OTHER INFORMATION: Antibody heavy chain

<400> SEQUENCE: 26

Met Asn Phe Gly Leu Ser Leu Ile Phe Leu Val Leu Val Leu Lys Gly
1               5                   10                  15

Val Gln Cys Asn Val Gln Leu Val Glu Ser Gly Gly Gly Leu Val Lys
            20                  25                  30

Pro Gly Gly Ser Leu Lys Leu Ser Cys Val Ala Ser Gly Phe Ile Phe
        35                  40                  45

Ser Asp Tyr Val Met Ser Trp Val Arg Gln Thr Pro Glu Lys Arg Leu
    50                  55                  60

Glu Trp Val Ala Thr Ile Ser Asp Gly Gly Ile Tyr Thr Ser Tyr Pro
65                  70                  75                  80

Asp Asn Ile Lys Gly Arg Phe Thr Ile Ser Arg Asp Asn Ala Asn Asn
                85                  90                  95

Lys Leu Tyr Leu Gln Met Ser His Leu Arg Ser Glu Asp Thr Ala Met
            100                 105                 110

Tyr Phe Cys Ser Arg Ala Ala Ile Thr Ser Asp Phe Asp Phe Trp
        115                 120                 125

Gly Gln Gly Thr Ala Leu Thr Val Ser Ser
    130                 135

<210> SEQ ID NO 27
<211> LENGTH: 119
<212> TYPE: PRT
<213> ORGANISM: Artificial Sequence
<220> FEATURE:
<223> OTHER INFORMATION: Antibody heavy chain

<400> SEQUENCE: 27

Asn Val Gln Leu Val Glu Ser Gly Gly Gly Leu Val Lys Pro Gly Gly
1               5                   10                  15

Ser Leu Lys Leu Ser Cys Val Ala Ser Gly Phe Ile Phe Ser Asp Tyr
            20                  25                  30

Val Met Ser Trp Val Arg Gln Thr Pro Glu Lys Arg Leu Glu Trp Val
        35                  40                  45

Ala Thr Ile Ser Asp Gly Gly Ile Tyr Thr Ser Tyr Pro Asp Asn Ile
```

```
                50                  55                  60
Lys Gly Arg Phe Thr Ile Ser Arg Asp Asn Ala Asn Lys Leu Tyr
 65                  70                  75                  80

Leu Gln Met Ser His Leu Arg Ser Glu Asp Thr Ala Met Tyr Phe Cys
                 85                  90                  95

Ser Arg Ala Ala Ile Thr Ser Asp Asp Phe Asp Phe Trp Gly Gln Gly
             100                 105                 110

Thr Ala Leu Thr Val Ser Ser
            115
```

```
<210> SEQ ID NO 28
<211> LENGTH: 5
<212> TYPE: PRT
<213> ORGANISM: Artificial Sequence
<220> FEATURE:
<223> OTHER INFORMATION: CDR region

<400> SEQUENCE: 28

Asp Tyr Val Met Ser
1               5

<210> SEQ ID NO 29
<211> LENGTH: 17
<212> TYPE: PRT
<213> ORGANISM: Artificial Sequence
<220> FEATURE:
<223> OTHER INFORMATION: CDR region

<400> SEQUENCE: 29

Thr Ile Ser Asp Gly Gly Ile Tyr Thr Ser Tyr Pro Asp Asn Ile Lys
1               5                   10                  15

Gly

<210> SEQ ID NO 30
<211> LENGTH: 10
<212> TYPE: PRT
<213> ORGANISM: Artificial Sequence
<220> FEATURE:
<223> OTHER INFORMATION: CDR region

<400> SEQUENCE: 30

Ala Ala Ile Thr Ser Asp Asp Phe Asp Phe
1               5                   10

<210> SEQ ID NO 31
<211> LENGTH: 13
<212> TYPE: PRT
<213> ORGANISM: Homo sapiens

<400> SEQUENCE: 31

Gln Arg Pro Arg Leu Ser His Lys Gly Pro Met Pro Phe
1               5                   10

<210> SEQ ID NO 32
<211> LENGTH: 7
<212> TYPE: PRT
<213> ORGANISM: Homo sapiens

<400> SEQUENCE: 32

Pro Arg Leu Ser His Lys Gly
1               5
```